United States Patent
Grafton et al.

[11] Patent Number: 5,964,783
[45] Date of Patent: Oct. 12, 1999

[54] SUTURE ANCHOR WITH INSERT-MOLDED SUTURE

[75] Inventors: R. Donald Grafton; Barton W. Bracy, both of Naples, Fla.

[73] Assignee: Arthrex, Inc., Naples, Fla.

[21] Appl. No.: 09/178,415

[22] Filed: Oct. 26, 1998

Related U.S. Application Data

[60] Provisional application No. 60/064,754, Nov. 7, 1997, provisional application No. 60/070,095, Dec. 31, 1997, and provisional application No. 60/078,393, Mar. 18, 1998.

[51] Int. Cl.[6] ................................................. A61B 17/04
[52] U.S. Cl. ............................................. 606/232; 606/72
[58] Field of Search ................................... 606/232, 288, 606/224, 139, 72, 151, 223, 138

[56] References Cited

U.S. PATENT DOCUMENTS

| | | | |
|---|---|---|---|
| 3,035,583 | 5/1962 | Hirsch et al. | 606/232 |
| 4,450,591 | 5/1984 | Rappaport | 623/21 |
| 4,884,572 | 12/1989 | Bays et al. | 606/139 |
| 5,102,421 | 4/1992 | Anspach, Jr. | 606/232 |
| 5,156,616 | 10/1992 | Meadows et al. | 606/232 |
| 5,370,661 | 12/1994 | Branch | 606/232 |
| 5,372,146 | 12/1994 | Branch | 606/232 |
| 5,520,691 | 5/1996 | Branch | 606/72 |
| 5,571,139 | 11/1996 | Jenkins, Jr. | 606/232 |
| 5,573,547 | 11/1996 | LeVeen et al. | 606/232 |

FOREIGN PATENT DOCUMENTS

| | | |
|---|---|---|
| 0464480 | 1/1992 | European Pat. Off. . |
| 0611557 | 8/1994 | European Pat. Off. . |
| 0632999 | 1/1995 | European Pat. Off. . |
| 0702933 | 3/1996 | European Pat. Off. . |
| 0778004 | 6/1997 | European Pat. Off. . |
| 9639082 | 12/1996 | WIPO . |
| 9710743 | 3/1997 | WIPO . |

*Primary Examiner*—Michael Buiz
*Assistant Examiner*—(Jackie)Tan-Uyen T. Ho
*Attorney, Agent, or Firm*—Ostrolenk, Faber, Gerb & Soffen, LLP

[57] ABSTRACT

An insert-molded suture anchor having a biodegradable polymer body molded around a loop of suture. A drive head disposed on the proximal end of the body, and a screw thread spirals around the body. The suture is held securely within the anchor body by forming irregularities in the braided suture used to form the anchor. The anchor is produced by placing the braided suture within an injection mold, and injecting biodegradable polymer into the mold.

10 Claims, 2 Drawing Sheets

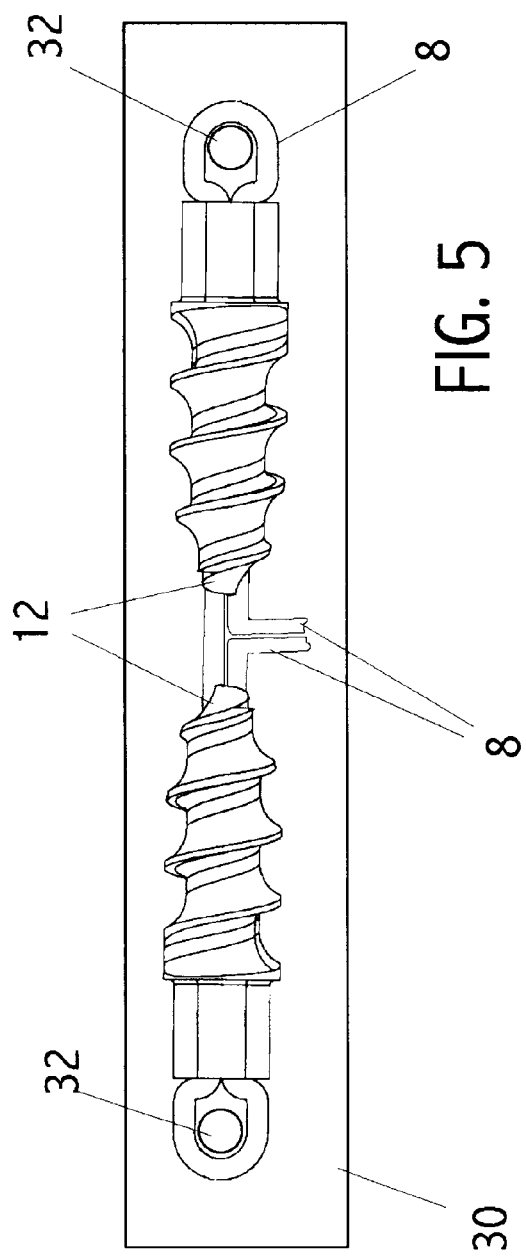
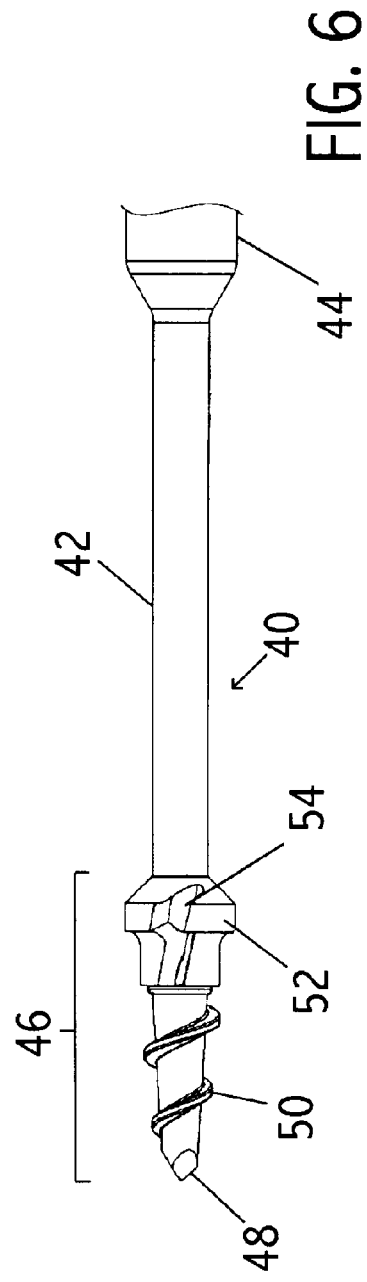

SUTURE ANCHOR WITH INSERT-MOLDED SUTURE

This application claims the benefit of U.S. Provisional Application Ser. No. 60/064,754, filed Nov. 7, 1997, U.S. Provisional Application Ser. No. 60/070,095, filed Dec. 31, 1997, and U.S. Provisional Application Ser. No. 60/078,393, filed Mar. 18, 1998, the disclosures of which are incorporated herein by reference.

BACKGROUND OF THE INVENTION

1. Field of the Invention

The present invention relates to an apparatus and method for anchoring surgical suture to bone. More specifically, the present invention relates to arthroscopic apparatus and methods for anchoring suture to bone using a suture anchor having suture molded directly into the suture anchor.

2. Description of the Related Art

When soft tissue tears away from bone, reattachment becomes necessary. Various devices, including sutures alone, screws, staples, wedges, and plugs have been used in the prior art to secure soft tissue to bone.

Recently, various types of threaded suture anchors have been developed for this purpose. Some threaded suture anchors are designed to be inserted into a pre-drilled hole. Other suture anchors are self-tapping.

U.S. Pat. No. 4,632,100 discloses a cylindrical threaded suture anchor. The suture anchor of the '100 patent includes a drill bit at a leading end for boring a hole in a bone, followed by a flight of threads spaced from the drill bit for securing the anchor into the hole created by the drill bit. U.S. Pat. No. 5,370,662 discloses a suture anchor having a flight of threads which extend to the tip of the anchor. U.S. Pat. No. 5,156,616 discloses a similar suture anchor having an axial opening for holding a knotted piece of suture.

All of the above-noted suture anchors include structure for attaching the suture to the anchor. U.S. Pat. No. 4,632,100, for example, discloses and claims a press-fitted disc and knot structure which secures the suture to the anchor. In other suture anchors, such as those disclosed in U.S. Pat. No. 5,370,662, the suture is passed through an eyelet located on the proximal end of the anchor.

Problems can arise if the structure for attaching the suture fails, allowing the suture to become detached from the anchor. Also, the suture often is exposed to abrasion or cutting by sharp or rough areas along the walls of the bone canal into which the anchor is inserted.

Moreover, the eyelet or, in the case of U.S. Pat. No. 4,632,100, the axial opening for receiving the disc to which the suture is knotted, is formed as part of the drive head of the known suture anchors. Combining these two functions in one structure often tends to weaken the drive head.

In addition, various other modifications to the drive head often are employed in connection with suture attachment. For example, recessed grooves may be formed on opposite sides of the drive head to receive and protect the suture from abrasive areas of the suture anchor tunnel or to facilitate mating between the anchor to the driver. In such cases, the drive head often must be made of a larger diameter to recover the mechanical strength lost from the removal of material relating to the suture-attachment or suture-protection modifications.

Further, the prior art suture anchors having eyelets extending from the proximal ends require countersinking of the eyelet below the bone surface to avoid having the patient's tissue abrade against the exposed eyelet. As a result, suture attached to the eyelet is vulnerable to abrasion by the bony rim of the countersunk hole into which the suture anchor is installed. In addition, in biodegradable prior art devices, the eyelet can degrade rapidly, causing the suture to become detached from the anchor prematurely.

Insert-molding of suture is known and has been used, for example, in a device for hemostatic puncture closure developed by Kensey Nash Corporation. Known as the Angio-Seal™ and marketed by Sherwood Medical Company, the device has a strand of absorbable suture molded into an absorbable rod. The device is inserted into an artery and is used to anchor a collagen sponge against the arterial wall. To date, however, insert-molding has not been contemplated or employed for the purpose of attaching suture to a suture anchor.

Accordingly, a need exists for a threaded suture anchor to which suture is secured effectively so as to prevent detachment of the suture. In addition, a need exists for suture anchors having eyelets that will not abrade tissue and do not require countersinking.

SUMMARY OF THE INVENTION

The suture anchor of the present invention overcomes disadvantages of the prior art, such as those noted above, by providing a threaded suture anchor having suture that is insert-molded directly into the suture anchor during the manufacturing process. At least one length of the insert-molded suture extends from the proximal end of the suture anchor body. Both the suture anchor and suture preferably are made with biodegradable materials.

According to a preferred embodiment, irregularities are formed along the surface of the suture, especially where it is molded inside the suture body, to increase pullout strength of the suture from the anchor body. The surface irregularities can be formed by various methods including incorporating a thick fiber into the weave of the suture or by tying knots in the suture.

The threaded suture anchor of the present invention has a central body, a distal end, and a proximal end. The body preferably tapers from the narrow distal end to terminate in a blunt or rounded proximal end. The proximal end of the suture anchor body preferably has a hexagonal drive head.

The insert-molded suture preferably extends through the entire length of the hex head and exits at the proximal end of the anchor. In a preferred embodiment of the invention, the suture forms a loop outside the proximal end of the anchor. Advantageously, the suture exits the suture anchor along the central axis of the anchor, which prevents suture abrasion by the wall of the bone tunnel into which the anchor is inserted.

Other features and advantages of the present invention will become apparent from the following description of the invention, which refers to the accompanying drawings.

BRIEF DESCRIPTION OF THE DRAWINGS

FIG. 5 is a plan view schematic of a pair of suture anchors being formed in an injection mold, according to the present invention.

FIG. 6 is an elevation of a tap used in the step of pre-forming a hole in bone according to a method of inserting the suture anchor of the present invention.

DETAILED DESCRIPTION OF THE PREFERRED EMBODIMENTS

Figure 1:
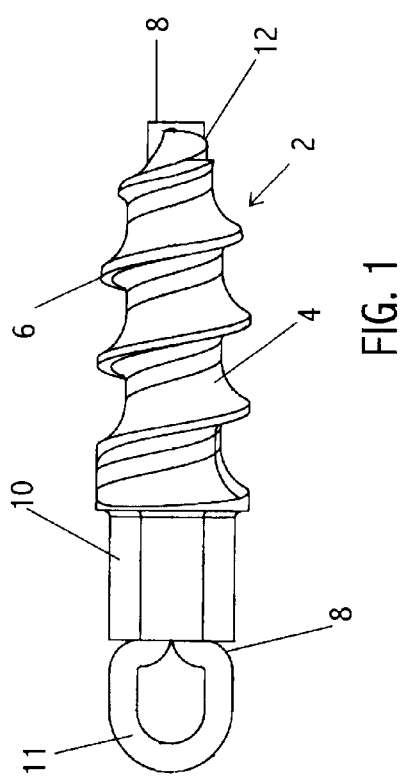
FIG. 1 is a plan view of a suture anchor according to the present invention.
Figure 2:
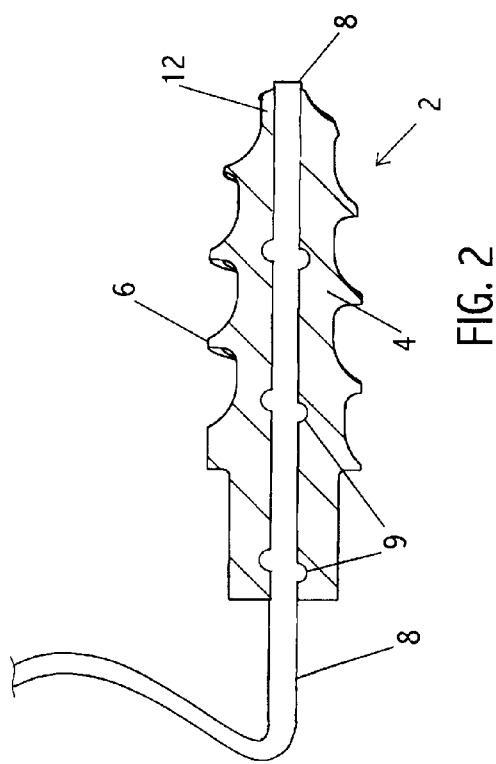
FIG. 2 is a sectional elevation of an alternative embodiment of the suture anchor of the present invention.

Referring to FIGS. 1 and 2, a suture anchor of the present invention, identified generally by reference numeral 2, includes a body 4 provided in the shape of a tapered cylinder. Suture anchor 2 is provided with a continuous thread 6 which wraps around body 4 in a clockwise direction, as shown.

A strand of suture 8, molded into the anchor body 4 during manufacture, preferably has irregular surface features 9 holding it within the molded body, as described more fully below. Suture 8 extends from the proximal end of the suture anchor. The suture passes out through a hexagonal drive head 10.

As shown in the embodiment of FIG. 1, the suture is formed into a loop 11 at the proximal end of the anchor. At the distal end 12, suture 8 is trimmed flush to provide a rounded tip. Alternatively, as shown in cross-section in the embodiment of FIG. 2, suture 8 can be left as a single strand, or multiple strands, extending from the proximal end of the anchor.

Figure 3:
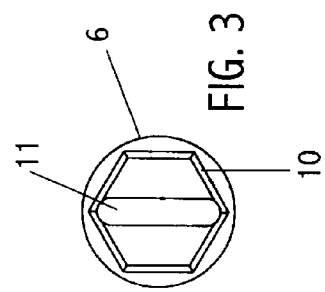
FIG. 3 is a proximal end view of the suture anchor of FIG. 1.

Referring to FIGS. 1 and 3, hexagonal drive head 10 is formed integrally with anchor body 4. At the junction between the hex drive head and the central body, the circumference of the central body is similar to the outer circumferential dimension of the hex drive head. Accordingly, the hex head possesses strength similar to that of the remainder of the suture anchor, i.e., the strength of the hex head is not compromised by the need to provide an eyelet for suture attachment.

Anchor body 4 preferably is formed of a translucent or transparent polymer material, and preferably is made of bioabsorbable materials such as polyglycolic or polylactic acid polymers. Accordingly, suture 8 is visible through the body of the anchor to provide visual confirmation of suture encapsulation within the anchor.

Advantageously, suture 8 and anchor body 4 are made of materials selected such that the suture loop 11 will not biodegrade before anchor body 4.

Figure 4:
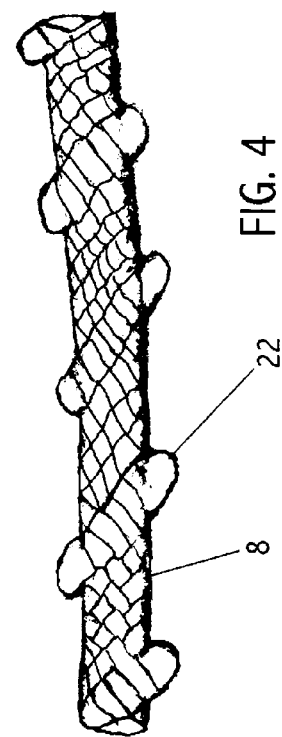
FIG. 4 is a plan view schematic of a suture strand having an irregular surface according to the present invention.

Referring to FIG. 4, an enlarged view of a portion of suture 8 having an irregular surface according to a preferred embodiment of the present invention is shown. The irregular surface is formed by weaving a larger-diameter suture filament 22 into the suture 8. The larger-diameter strand spirals around the suture to create the irregularities. The irregularities also may be formed by various other methods, such as braiding one or more of the suture filaments more loosely than the remaining suture filaments, or by forming knots. The magnitude of the surface irregularities is selected such that sufficient pullout strength is achieved without sacrificing the mechanical strength and integrity of the suture anchor body. Alternatively, or in addition, an adhesive can be applied to the suture prior to molding. The adhesive may be activatable by the molding process, thermally, photochemically, or otherwise.

Referring to FIG. 5, the anchors of the present invention preferably are formed in a mold 30 formed such that the distal tips 12 of two anchors 2 formed in the mold will face toward each other. FIG. 5 shows schematically an open mold in plan view and containing two fully-formed suture anchors.

During manufacture, a strand of irregular suture 8 is positioned in the mold in a T-shaped continuous loop. Pins 32 are provided in mold 30 to aid in positioning the suture and to form loops 11. After the suture is positioned, the mold is closed, and polymer is injected into the mold cavities through a gate, not shown. When the polymer has cured, the hardened anchors are removed from the mold. The two suture anchors are separated by cutting the suture 8 between the distal tips of the anchors. The suture is trimmed flush with the distal tip of each anchor.

Suture anchors according to the present invention can be used for arthroscopic procedures. The anchors also are advantageous for open and mini-open surgical procedures. Specific examples of applicable procedures include cortical bone-soft tissue fixation, Bankart and SLAP shoulder repairs. Suture anchor 2 can be made in various sizes, typically on the order of about 2.4 to 2.9 mm in diameter.

The preferred surgical method generally includes pre-forming a hole using a tap 40 as shown in FIG. 6 and described more fully below, and inserting the insert-molded suture anchor into the pre-formed hole. The anchor then is engaged with a driver and turned to advance the suture anchor into the bone. Alternatively, a self-drilling/self-tapping suture anchor can be formed and inserted directly into bone by engaging the anchor with a driver and turning the anchor to advance the anchor directly into bone without previous formation of a hole.

FIG. 6 shows a preferred tap 40 for forming a hole in bone into which suture anchor 2 is to be inserted. Tap 40 includes a shaft 42 having a handle 44 (partially shown) on a proximal end and a tapping head 46 on a distal end. Tapping head 46 includes a trocar tip 48 followed by a tapered, spiral cutting section 50. Proximal to the spiral cutting section, a countersink-forming section 52 is provided with a cutting edge 54.

Using tap 40, a hole for the suture anchor includes a countersink formed in the bone surface to accommodate a head formed on the distal end of a cannulated driver used to install the suture anchor. The head of the driver fits over hex head 10 of anchor 2. An outer diameter of the driver head extends beyond the outer thread diameter of the suture anchor and the spiral cutting section of the tap. Accordingly, it is necessary to form a countersink so that the suture anchor can be installed flush with the surface of the bone.

When installing the suture anchor into bone, it is not necessary for the proximal end of the anchor to be counter-sunk below the bone surface, as is required with prior art devices to prevent tissue abrasion by the exposed eyelet. Consequently, the inventive anchor does not need to be inserted as far as prior art devices, and avoids abrasion of suture by the rim of bone. Friction between the eyelet and the suture, which can abrade the suture, also is avoided, in contrast to prior art devices.

Additionally, due to its flexible nature, the eyelet can be formed larger than on prior art suture anchors. Consequently, the suture anchor of the present invention is able to accommodate larger or multiple strands of suture. Moreover, the present suture anchor allows attachment suture to slide through the suture loop with reduced friction, as compared to prior art suture anchors.

The suture anchors of the present invention provide greater pull-out strength of the eyelet than prior suture anchors. In addition, the strength of the eyelet does not degrade as the anchor degrades. Also, by selection of materials used for the suture loop and the anchor, the degradation profiles of the suture loop and the anchor can be selected according to the needs of the particular procedure being performed. Also, the strength of the suture attachment to the anchor does not degrade as the anchor degrades.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A suture anchor formed by a process comprising the steps of:

placing at least one piece of suture in a mold;

molding a suture anchor body around the suture by delivering an uncured polymer into the mold; and causing the polymer to cure.

2. The suture anchor of claim 1, wherein irregularities are formed in the surface of the suture to anchor the suture within the suture anchor body.

3. The suture anchor of claim 2, wherein the irregularities comprise knots formed in the suture.

4. The suture anchor of claim 2, wherein the suture is woven from a plurality of fibers, and the irregularities comprise at least one fiber having a diameter greater than the remaining fibers woven into the suture.

5. The suture anchor of claim 1, wherein the suture anchor body has a proximal end, and the suture forms a loop outside the proximal end of the suture anchor body.

6. A method of producing an insert-molded suture anchor, the method comprising the steps of:

placing at least one piece of suture in a mold;

molding a suture anchor body around the suture by delivering an uncured polymer into the mold; and causing the polymer to cure.

7. The method of claim 6, further comprising the step of forming at least one irregularity in the portion of suture placed within the mold.

8. The method of claim 6, wherein the suture has opposing sections, and the suture is placed in the mold such that the opposing sections extend respectively from opposing ends of the cured suture anchor body.

9. The method of claim 6, wherein the suture anchor is threaded.

10. The method of claim 6, wherein the suture is placed in the mold so as to form a loop at the proximal end of the suture anchor.

* * * * *